United States Patent
Zhang et al.

(10) Patent No.: US 6,812,248 B2
(45) Date of Patent: Nov. 2, 2004

(54) PREVENTION AND TREATMENT OF DEGENERATIVE DISEASES BY GLUTATHIONE AND PHASE II DETOXIFICATION ENZYMES

(75) Inventors: Yuesheng Zhang, Tucson, AZ (US); Tony W. Ho, Malvern, PA (US); Yun Li, Tucson, AZ (US)

(73) Assignee: John Hopkins University School of Medicine, Baltimore, MD (US)

( * ) Notice: Subject to any disclaimer, the term of this patent is extended or adjusted under 35 U.S.C. 154(b) by 106 days.

(21) Appl. No.: 09/897,934

(22) Filed: Jul. 5, 2001

(65) Prior Publication Data

US 2002/0091087 A1 Jul. 11, 2002

Related U.S. Application Data

(60) Provisional application No. 60/215,812, filed on Jul. 5, 2000.

(51) Int. Cl.$^7$ .............................................. A61K 31/21
(52) U.S. Cl. ...................................... 514/514; 514/474
(58) Field of Search ................................ 514/514, 474

(56) References Cited

U.S. PATENT DOCUMENTS

| | | |
|---|---|---|
| 5,780,489 A | 7/1998 | Brooks |
| RE36,784 E | 7/2000 | Cho et al. |
| 6,184,248 B1 * | 2/2001 | Lee et al. .................. 514/474 |
| 6,469,055 B2 * | 10/2002 | Lee et al. .................. 514/474 |

FOREIGN PATENT DOCUMENTS

| | | |
|---|---|---|
| WO | WO 98/29375 A1 | 7/1998 |
| WO | WO 01/47469 A2 | 7/2001 |

OTHER PUBLICATIONS

Frankel et al., Cysteamine Pretreatment of the Astroglial Substratum (Mitochondrial Iron Sequestration) Enhances PC12 Cell Vulnerability to Oxidative Injury, Experimental Neurology 160: 376–385 (1999).*

Offen et al., "Prevention of Dopamine–Induced Cell Death by Thiol Antioxidants: Possible Implications for Treatment of Parkinson's Disease," *Experimental Neurology* (1996), vol. 141, pp. 32–39, XP00106489, ISSN: 0014–4886.

Hurd et al., "Treatment of four siblings with progressive myoclonus epilepsy of the Unverricht–Lundborg type with N–acetylcysteine," *Neurology* (Nov. 1996), vol. 47, pp. 1264–1268, American Academy of Neurology, XP001064864, ISSN: 0028–3878.

Martínez et al., "Hypothesis: Can N–Acetycysteine be Beneficial in Parkinson's Disease," *Life Sciences* (1999), vol. 64, No. 15, pp. 1253–1257, Elsevier Science Ltd., XP001064840, ISSN: 0024–3205.

Uthman et al, :"N–Acetylcysteine in the Treatment of Five Siblings with Hereditary Spinocerebellar Ataxia," *Neurology* (1995), vol. 45, No. 4, Suppl. 4, pp. A185–A186, 47$^{th}$ Annual Meeting of the American Academy of Neurology, Seattle, Washington, XP001064863, ISSN: 0028–3878, abstract.

Jakoby et al. *J. Biol. Chem.* 265:20715–20718 (Dec., 1990).
Conney et al. *Fed. Proc. Fed. Am. Soc. Exp. Biol.* 36:1647–1652 (Apr., 1977).
Sparnins et al. *J. Natl. Cancer Inst.* 66:769–771 (Apr., 1981).
Sparnins et al. *J. Natl. Cancer Inst.* 68:493–496 (Mar., 1982).
Aspry et al. *Food Chem. Toxicol.* 21:133–142 (Apr., 1983).
Bradfield et al. *Food Chem. Toxicol.* 23:899–904 (Oct., 1985).
Salbe et al. *Food Chem. Toxicol.* 24:851–856 (Apr., 1986).
Whitty et al. *Food Chem. Toxicol.* 25:581–587 (Aug., 1987).
Ansher et al. *Hepatology* 3:932–935 (Nov., 1983).
Ansher et al. *Food Chem. Toxicol.* 24:405–415 (May, 1986).
Pantuck et al.*Clin. Pharmacol. Ther.* 25:88–95 (Jan., 1979).
Pantuck et al. *Clin. Pharmacol. Ther.* 35:161–169 (Feb., 1984).
Tannenbaum et al. *Adv. Cancer Res.,* Grenenstein, JP and Haddow, A, eds. 1:451–501, Academic Press, New York, NY (1953).
Masliah et al. *J. Neurosci.* 16:5795–5811 (Sep., 1996).
Eckert et al. *J. Neurosci. Res.* 64(2):183–192 (Apr., 2001).
Takahashi et al. *Neuron.* 28(2):461–473 (Apr., 2000).
Longnecker et al. *Cancer.* 1562–1572 (Mar., 1981).
Fullerton et al. *Proc. Am. Assoc. Cancer Res.* 29:147 (Abst. 585) (Mar., 1988).
Li et al. *Cancer Res.* 50:3991–3996 (Jul., 1990).
Favreau et al. *J. Biol. Chem.* 266:4556–4561 (Mar., 1991).
Fahey et al. *Phytochemistry* 56:5–51 (Jan., 2001).
Talalay. *Biofactors* 12:5–11 (2000).
Prestera et al. *Mol. Med.* 1:827–837 (Nov., 1995).
Primiano et al. *Carcinogenesis* 17:2291–2296 (Nov., 1996).
Hensley et al. *J. Neurochem* 65(5):2146–2158 (Nov., 1995).
Mecocci et al. *Ann Neurol.* 36(5):747–751 (Nov., 1994).
Palmer et al. *Brain Res.* 645(1–2):338–342 (May, 1994).
Lovell and Markesbery.*Arch. Neurol.* 58(3):392–396 (Mar., 2001).

(List continued on next page.)

*Primary Examiner*—Jean C. Witz
(74) *Attorney, Agent, or Firm*—Foley & Lardner (57) ABSTRACT

The present invention generally relates to the field of treating degenerative disease by administering a pharmaceutically effective amount of a compound that elevates glutathione or at least one Phase II detoxification enzyme in diseased tissue. The present invention also relates to a pharmaceutical composition useful for the treatment of degenerative diseases, as well as a method of identifying agents that modulate intracellular levels of glutathione or intracellular levels of at least one Phase II enzyme in neuronal cells.

6 Claims, 5 Drawing Sheets

OTHER PUBLICATIONS

Aksenov et al. *Neuroscience* 103(2):373–383 (2001).
Behl et al. *Cell.* 77(6):817–827 (Jun., 1994).
Varadarajan et al. *J. Struct. Biol.* 130(2–3):184–208 (Jun., 2000).
Markesbery. *Arch. Neurol.* 56(12):1449–1452 (Dec., 1999).
Pappolla et al. *Am. J. Pathol.* 152(4):871–877 (Apr., 1998).
Smith et al. *J. Neurochem.* 70(5):2212–2215 (May, 1998).
Sano et al. *N. Engl. J. Med.* 336(17):1216–1222 (Apr., 1997).

* cited by examiner

PREVENTION AND TREATMENT OF DEGENERATIVE DISEASES BY GLUTATHIONE AND PHASE II DETOXIFICATION ENZYMES

This application claims the benefit of U.S. Provisional Application No. 60/215,812, filed Jul. 5, 2000 under 35 USC 119(e).

STATEMENT AS TO THE RIGHTS TO INVENTIONS MADE UNDER FEDERALLY SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention generally relates to the field of treating degenerative disease by administering a pharmaceutically effective amount of a compound that elevates glutathione or at least one Phase II detoxification enzyme in diseased tissue. The present invention also relates to a pharmaceutical composition useful for the treatment of degenerative diseases, as well as a method of identifying agents that modulate intracellular levels of glutathione or intracellular levels of at least one Phase II enzyme in neuronal cells.

2. Background of the Invention

Enzymes of xenobiotic biotransformation belong to two families: Phase I enzymes (cytochromes P-450), which usually oxidize or reduce xenobiotics. Although their primary role is to detoxify xenobiotics, cytochromes P-450 may also generate highly reactive and toxic compounds (Miller, et al., Bioactivation of Foreign Compounds, 3–28 (1985)). The second family of xenobiotic transformative enzymes is Phase II enzymes, which usually conjugate an endogenous moiety (e.g., glutathione, sulfate) to the xenobiotic, and serve primarily a detoxification role (Jakoby, et al., J. Biol. Chem. 265:20715–20718 (1990)). Phase II enzymes are generally induced in a coordinated fashion in response to xenobiotics. Quinone reductase (QR) is also considered a Phase II enzyme because it has protective functions (Prochaska, et al., Oxidative Stress: Oxidants and Antioxidants, 195–211 (1991)), is induced coordinately with other Phase II enzymes, and is regulated by enhancer elements similar to those that control glutathione transferase (Favreau, et al., J. Biol. Chem. 266:4556–4561 (1991)).

Well-documented evidence established that feeding of certain vegetables (e.g., brussels sprouts and cabbage) modulates both Phase I and Phase II enzymes in animal tissues (Conney, et al., Fed. Proc. Fed. Am. Soc. Exp. Biol. 36:1647–1652 (1977); Sparnins, et al., J. Natl. Cancer Inst. 66:769–771 (1981); Sparnins, et al., J. Natl. Cancer Inst. 68:493–496 (1982); Aspry, et al., Food Chem. Toxicol. 21:133–142 (1983); Bradfield, et al., Food Chem. Toxicol. 23:899–904 (1985); Salbe, et al., Food Chem. Toxicol. 24:851–856 (1985); Whitty, et al., Food Chem. Toxicol. 25:581–587 (1987); Ansher, et al., Hepatology 3:932–2935 (1983); Ansher, et al., Food Chem. Toxicol. 24:405–415 (1986)) and stimulates the metabolism of drugs in humans (Conney, et al., Fed. Proc. Fed. Am. Soc. Exp. Biol. 36:1647–1652 (1977); Pantuck, et al., Clin. Pharmacol. Ther. 25:88–95 (1979); Pantuck, et al., Clin. Pharmacol. Ther. 35:161–169 (1984)). The elevations of enzymes that metabolize xenobiotics and scavenge free-radicals may be highly relevant to the chemoprotective effects of vegetables, since relatively modest dietary changes not only affects the metabolism of drugs (Ansher, et al., Food Chem. Toxicol. 24:405–415 (1986)) but also modifies the ability of carcinogens to cause tumors in rodents (Tannenbaum, et al., Adv. Cancer Res. 1:451–501 (1953); National Research Council, Diet, Nutrition and Cancer (1982); National Research Council, Diet and Health: Implications for Reducing Chronic Disease Risk (1989); Creasey, Diet and Cancer (1985); Knudsen, Genetic Toxicology of the Diet (1986); Longnecker, et al., Cancer 47:1562–1572 (1981); Fullerton, et al., Proc. Am. Assoc. Cancer Res. 29:147 (1988); Li, et al., Cancer Res. 50:3991–3996 (1990)).

In degenerative diseases, which are generally characterized by progressive morphological changes and progressive loss in normal metabolic activity in the cells of the tissue, it is believed that oxidative stress may play an important role in the etiology of the diseases. Thus anti-oxidants, which function to scavenge free-radicals and thereby prevent oxidative damages to cells, may provide an opportunity to treat or prevent the progression of degenerative diseases. Additionally, if a treatment can act as an anti-oxidant to the cells, as well as induce Phase II enzymes, which also protect the cell from free radicals, this treatment would provide a two-pronged attack on the progression of degenerative diseases. To date, no such compounds have been identified.

SUMMARY OF THE INVENTION

The invention relates to a method of treating a subject in need of treatment of a degenerative disease, which comprises administering to the subject a pharmaceutically effective amount of a compound that elevates glutathione, or at least one Phase II detoxification enzyme, in the diseased tissue of the subject.

The invention also relates to a method of inhibiting cell death in neuronal cells, which comprises treating the neuronal cells with an agent that increases levels of glutathione, or intracellular levels of at least one Phase II detoxification enzyme.

The invention also relates to a method of identifying agents that modulate intracellular levels of glutathione or intracellular levels of at least one Phase II enzyme in neuronal cells, which comprises treating the neuronal cells with an agent, assaying for intracellular levels of glutathione or intracellular levels of at least one Phase II detoxification enzyme, and comparing these levels to control levels.

The invention also relates to a method of identifying agents that modulate intracellular levels of glutathione or intracellular levels of at least one Phase II enzyme in neuronal cells comprising comparing the levels of the intracellular glutathione or intracellular levels of at least one Phase II detoxification enzyme to determine if the agent modulates intracellular levels of glutathione or intracellular levels of at least one Phase II detoxification enzyme.

The invention also relates to a method of modulating intracellular levels of at least one Phase II detoxification enzyme in neuronal cells. The method comprises treating the neuronal cells with an agent that binds to glutathione to form a complex. The complex modulates the intracellular levels of at least one Phase II detoxification enzyme.

The invention also relates to a composition for use in the treatment of a degenerative disease, which comprises a pharmaceutical excipient and a pharmaceutically effective amount of an agent that increases intracellular levels of glutathione or at least one Phase II detoxification enzyme.

DETAILED DESCRIPTION OF THE PREFERRED EMBODIMENTS

The present invention relates to a method of treating a subject in need of treatment of a degenerative disease, the method comprising administering to the subject a pharmaceutically effective amount of a compound that elevates levels intracellular glutathione or intracellular levels of at least one Phase II detoxification enzyme in diseased tissue of said subject.

As used herein, the term subject can be used to mean an animal, preferably a mammal including a human or non-human. The term patient is used to indicate a subject in need of treatment of a degenerative disease. Furthermore, the terms "disease," "condition" and "disorder" may all be used interchangeably.

The current invention can be useful in treating a subject in need of treatment of a degenerative disease where there may be aberrant levels of glutathione or any Phase II enzyme present in the diseased cells or tissue. These abnormal levels may be either causal or symptomatic of the degenerative disease. The phrase "degenerative disease," as used in the current context, should be obvious to one of ordinary skill in the art, but is used to mean any physiological condition that may be characterized by the death of normal cells in the affected tissue. As used herein a degenerative disease is not used to mean a disease where the death of the normal cells is caused by tumor growth or acute toxic insult. Examples of degenerative disorders for which the current invention can be used preferably include, but are not limited to, diabetes, chronic liver failure, chronic kidney failure, Wilson's disease, congestive heart failure and atherosclerosis and any neurodegenerative disease.

A neurodegenerative disease, as used in the current context, should be obvious to one skilled in the art, but is meant to include any abnormal physical or mental behavior or experience where the death of neuronal cells is involved in the etiology of the disorder, or is affected by the disorder. As used herein, neurodegenerative diseases encompass disorders affecting the central and peripheral nervous systems, and include such afflictions as memory loss, stroke, dementia, personality disorders, gradual, permanent or episodic loss of muscle control. Examples of neurodegenerative diseases for which the current invention can be used preferably include, but are not limited to, Alzheimer's Disease, Parkinson's Disease, Huntington's Disease, amyotrophic lateral sclerosis, epilepsy, myasthenia gravis, neuropathy, ataxia, dementia, chronic axonal neuropathy and stroke.

The treatment envisioned by the current invention can be used for patients with a pre-existing degenerative condition, or for patients pre-disposed to a degenerative disorder. Additionally, the method of the current invention can be used to correct cellular or physiological abnormalities involved with a degenerative disorder in patients, and/or to alleviate symptoms of a degenerative disorder in patients, or as a preventative measure in patients.

As used herein, the term agent or compound is intended to mean a protein, nucleic acid, carbohydrate, lipid, polymer or a small molecule, such as a drug. The types of agents or compounds which can be envisioned are limited only by their ability to elevate intracellular levels of glutathione or Phase II enzymes.

As used herein, "a pharmaceutically effective amount" is intended used to mean an amount effective to elicit a cellular response that is clinically significant, without excessive levels of side effects.

The present invention relates to methods of elevating intracellular glutathione (GSH) as a way to prevent or treat degenerative diseases. GSH is a tripeptide composed of glycine, cysteine and glutamate, with the glutamate being linked to cysteine via the gamma-carboxyl group (as opposed to an alpha-carboxyl linkage that normally occurs in a peptide). GSH is a detoxifying peptide that the body conjugates to xenobiotics (foreign chemical or compound) to render the xenobiotic more hydrophilic, thus promoting their excretion from the body. The synthesis of GSH involves a two-step reaction, with the first being catalyzed by gamma-glutamylcysteine synthetase. Glutathione synthetase catalyzes the second reaction. In turn, the conjugation of GSH to the xenobiotic is catalyzed by glutathione S-transferase (also referred to as GSH transferase), which can be a dimer of identical (homodimer) or different (heterodimer) subunits, although some heterodimers do exist. To date, at least four classes of GSH transferases have been identified, with each class having two or more types of subunits therein. Most GSH transferases are cytosolic (or soluble), meaning they are found in a cell's cytosol, although at least two microsomal GSH transferases exist. Based on such factors as amino acid similarity and biological activity, one of ordinary skill in the art will be able to appreciate and recognize the many types of GSH transferases that exist, as well as any that may not yet be identified. Thus, as used herein, the phrases "increase in intracellular GSH" or "elevation in intracellular GSH" is intended to mean the GSH tripeptide itself, as well as the enzymes responsible for its synthesis and conjugation to xenobiotics.

The present invention also relates to a method increasing the intracellular levels of at least one Phase II detoxification enzyme. The phrases "Phase II detoxification enzyme" and "Phase II enzyme" are used interchangeably herein. As used herein, a Phase II enzyme is any enzyme that is involved in any of the Phase II reactions which are responsible for the biotransformation of xenobiotics and/or prevention of oxidative stress. Generally speaking, a Phase II reaction will generally involve the conjugation of a moiety to the xenobiotic that will increase the hydrophilicity of the xenobiotic. This conjugated xenobiotic, which is now more hydrophilic, is more readily excreted from the body, than the unconjugated xenobiotic. There are six types of Phase II conjugation reactions, including glucuronidation, sulfation, methylation, acetylation, amino acid conjugation and glutathione conjugation. The reaction catalyzed by the enzyme rhodanese (the transfer of a sulfur ion to cyanide to form thiocyanate) will also be considered a Phase II reaction herein.

Briefly, glucuronidation is a major pathway of xenobiotic transformation and involves the conjugation of glucuronide to the xenobiotic. The reaction is catalyzed by UDP-glucuronosyltransferase (UDPGT), of which multiple forms exist. These multiple forms are encoded by several different genes. One of ordinary skill in the art will be able to recognize and appreciate the different forms of UDPGT, and the reactions they catalyze.

Sulfation is a pathway of xenobiotic transformation that involves the conjugation of sulfate to the xenobiotic. The reaction is catalyzed by sulfotransferases, of which more than a dozen forms have been identified. One of ordinary skill in the art will be able to recognize and appreciate the different forms of sulfotransferases, and the reactions they catalyze.

Methylation is a pathway of xenobiotic transformation that involves the conjugation of a methyl group to the xenobiotic. There are three different methylation reactions, based on the type of atom on the xenobiotic that is methylated. The three methylation reactions can occur on, sulfur (S), oxygen (O) and nitrogen (N), each of which is catalyzed by a different sets of enzymes. O-methylation is catalyzed by phenol-O-methyltransferase (POMT) or catechol-O-methyltransferase (COMT). It is believed that COMT is encoded by a single gene, with at least two different allelic variants. N-methylation is catalyzed by histamine-N-methyltransferase or nicotinamide-N-methyltransferase. S-methylation is catalyzed by at least two enzymes, including thiopurine methyltransferase (TPMT) and thiol methyltransferase (TMT). One of ordinary skill in the art will be able to recognize and appreciate the different forms of methlytransferases, and the reactions they catalyze.

Acetylation is a pathway of xenobiotic transformation that involves the conjugation of an acetyl group to the xenobiotic. There are two different acetylation reactions, based on the type of atom (O and N) on the xenobiotic that is acetylated. The two acetylation reactions may or may not be catalyzed by the same set of enzymes. N-acetylation is catalyzed by N-acetyltransferase (NAT), of which two forms exist in humans. These forms are encoded by two different genes. O-acetylation is catalyzed by O-acetyltransferase, but may also be catalyzed by NAT. One of ordinary skill in the art will be able to recognize and appreciate the different forms of acetyltransferases, and the reactions they catalyze.

Amino acid conjugation is a pathway of xenobiotic transformation that involves the conjugation of an amino acid to the xenobiotic. There are two principle pathways where amino acids are conjugated to xenobiotics. The first reaction involves xenobiotics containing a carboxylic acid. This reaction takes place by acyl-CoA synthetase catalyzing the conjugation of CoA to the xenobiotic to form a thioester. The thioester is subsequently conjugated to the amino acid via the acyl-CoA:amino acid N-transferase enzyme. The second principle pathway where xenobiotics are conjugated to amino acids involves xenobiotics containing an aromatic hydroxylamine. This reaction involves the activation of an amino acid with the aminoacyl-tRNA-sythetase. The activated amino acid subsequently reacts with the aromatic hydroxylamine on the xenobiotic to form a reactive N-ester. One of ordinary skill in the art will be able to recognize and appreciate the different types of enzymes responsible for the conjugation of amino acids to xenobiotics, and the reactions they catalyze. Quinone reductase (QR) is considered a Phase II enzyme because it has protective functions (Prochaska, et al., Oxidative Stress: Oxidants and Antioxidants, 195–211 (1991)), is induced coordinately with other phase II enzymes, and is regulated by enhancer elements similar to those that control glutathione transferase (Favreau, et al., J. Biol. Chem. 266:4556–4561 (1991)).

Heme oxygenase (HO), also considered a Phase II enzyme, catalyzes the conversion of heme to biliverdin, which is subsequently reduced to bilirubin. Thus the HO enzyme is responsible for the production of bilirubin, which itself is a powerful antioxidant. Additionally, the HO enzyme is induced by many of the same compounds that induce other Phase II enzymes.

Examples of additional Phase II enzymes include, but are not limited to, such enzymes as glutathione reductase, glutathione peroxidase, catalase and superoxide dismutase.

The present invention relates to increasing the levels of at least one Phase II enzyme in diseased tissue. It is possible that the compounds contemplated in this invention may be responsible for the increase levels of only one of the Phase II enzymes, or more than one Phase II enzyme. As used herein, the phrase "increase in levels of Phase II enzymes" is used to mean an increase in the quantity of Phase II enzymes present in the cell, compared to control (non-stimulated) levels. The phrase is also used to mean an increase in the activity or specificity of the enzymes present in the cell.

As used herein, the term diseased tissue may be used to mean individual cells, as cultured in vitro, or excised tissue in whole or in part. Diseased tissue may also be used to mean tissue in the subject that is undergoing the degenerative process, or tissue within the same organ 11 that may not yet be affected by the degenerative process. The normal tissue may or may not be adjacent to the degenerative tissue.

As a preferred embodiment, the compounds used in the methods of the current invention that elevate glutathione or any Phase II enzyme, are selected from the group consisting of a glutathione precursor, an isothiocyanate and a glucosinolate. Glutathione precursors include N-acetylcysteine.

Isothiocyanates are compounds containing the thiocyanate (SCN) moiety and are easily identifiable by one of ordinary skill in the art. An example of an isothiocyanate includes, but is not limited to sulforaphane or its analogs. The description and preparation of isothiocyanate analogs is described in United States Reissue Patent 36,784, and is hereby incorporated by reference in its entirety. In a preferred embodiment, the sulforaphane analogs used in the present invention include 6-isothiocyanato-2-hexanone, exo-2-acetyl-6-isothiocyanatonorbornane, exo-2-isothiocyanato-6-methylsulfonyinorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3-(methylsulfonyl)cyclohexylmethylisothiocyanate and trans-3-(methylsulfonyl)cyclohexylmethylisothiocyanate.

Glucosinolates, which are well-known in the art, are precursors to isothiocyanates. Glucosinolates are easily recognizable and appreciated by one of ordinary skill in the art and are reviewed in Fahey et al. Phytochemistry, 56:5–51 (2001), the entire contents of which are hereby incorporated by reference.

Other compounds contemplated by the present invention include compounds that are known to induce (increase) levels of Phase II enzymes. Preferably, these compounds include resveratrol, oltipraz, dimethylfumarate, 2(3)-tert-butyl-4-hydroxyanisole, 3,5-di-tert-butyl-4-hydroxytoluene and an analog thereof.

The present invention also provides a method of inhibiting cell death in neuronal cells comprising treating said neuronal cells with an agent that increases intracellular levels of glutathione or intracellular levels of at least one Phase II detoxification enzyme. As contemplated by the current invention, "cell death" is used to mean a process or event that causes the cell to cease or diminish normal metabolism in vivo or in vitro. The various forms and signs of cell death are obvious to those skilled in the art, but examples of cell death include, but are not limited to, programmed cell death (i.e., apoptosis), gradual death of the cells as occurs in diseased states (i.e., necrosis), and more immediate cell death such as acute toxicity. The inhibition of cell death for which the current invention provides can be a complete or partial inhibition of cell death. Likewise, the inhibition of cell death for which the current invention provides can be a complete or partial reversal of the process of cell death.

As used herein, neuronal cells include cells of the central and peripheral nervous systems, including the two classes of neurons and glial cells. Within each class of cells, there are unique types of cells that one of ordinary skill in the art would recognize such as oligodendrocytes, astrocytes and Shwann cells belonging to the glial cell class.

As a preferred embodiment, the method of inhibiting neuronal cell death of the current invention can be accomplished by treating the cell with an agent that is selected from the group consisting of a glutathione precursor, an isothiocyanate and a glucosinolate. More preferably, the isothiocyanate is selected from the group consisting of sulforaphane and a sulforaphane analog.

Preferably, the sulforaphane analogs to be used for preventing neuronal cell death are selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'hydroxyethyl)-5-isothiocyanatonorbornane, exo-2-acetyl-5-isothiocyanatonorbornane, 1-isothiocyanato-5-methylsulfonylpentane, cis-3-(methylsulfonyl)cyclohexylmethylisothiocyanate and trans-3-(methylsulfonyl)cyclohexylmethylisothiocyanate.

Other compounds may be used to prevent neuronal cell death by increasing the levels of glutathione or Phase II enzymes. In another preferred embodiment, those compounds are selected from the group consisting of resveratrol, oltipraz, dimethylfumarate, 2(3)-tert-butyl-4-hydroxyanisole, 3,5-di-tert-butyl-4-hydroxytoluene and an analog thereof.

The Phase II enzymes that are to be elevated by the methods of the current invention to prevent neuronal cell death have been previously described herein.

The current invention also provides a method of identifying agents that modulate intracellular levels of glutathione or intracellular levels of at least one Phase II enzyme in neuronal cells comprising (a) treating said neuronal cells with an agent, and assaying for intracellular levels of glutathione or intracellular levels of at least one Phase II detoxification enzyme; (b) treating said neuronal cells with a known modulator of intracellular levels of glutathione or intracellular levels of at least one Phase II detoxification enzyme (control substance), and assaying for intracellular levels of glutathione or intracellular levels of at least one Phase II detoxification enzyme and (c) comparing the levels of said intracellular glutathione or intracellular levels of at least one Phase II detoxification enzyme in (a) and (b) to determine if said agent modulates intracellular levels of glutathione or intracellular levels of at least one Phase II detoxification enzyme.

In one embodiment of the current invention, the method of identifying an agent that modulates intracellular levels of glutathione or Phase II enzymes in neuronal cells is performed on a single population of cells, and (b) is performed on the identical population after the agent in (a) is removed. In another embodiment of the invention, the method of identifying an agent that modulates intracellular levels of glutathione or Phase II enzymes in cells is performed on two nearly identical populations of cells, under the same culture conditions, where (a) is performed on one population and (b) is performed on another population, and (c) is a comparison of the levels of intracellular levels of glutathione or Phase II enzymes between the two populations of cells.

As used herein, assaying for intracellular levels of glutathione or Phase II enzymes can be accomplished by using any means that can detect differences in intracellular or extracellular intracellular levels of glutathione or Phase II enzymes. Such means, which should be obvious to one of ordinary skill on the art.

As used herein, modulation of intracellular glutathione or any intracellular Phase II enzyme of the affected cell includes such responses as increasing or decreasing the levels of glutathione or any Phase II enzyme that are normally up-regulated or down-regulated in the cell, in response to another stimulus. Likewise, modulation of intracellular glutathione or any intracellular Phase II enzyme in the affected cell also includes such responses as increasing or decreasing the levels of glutathione or any Phase II enzyme that are normally present in the cell, in the absence of another stimulus. Additionally, modulation of intracellular glutathione or any intracellular Phase II enzyme is meant to encompass increasing or decreasing the quantity of release or uptake of glutathione or any Phase II enzyme from or to intracellular stores, such as mitochondria, in conjunction with another stimulus. Likewise, modulation of intracellular glutathione or any intracellular Phase II enzyme is also meant to encompass increasing or decreasing the quantity of release or uptake of glutathione or any Phase II enzyme from or to intracellular stores, such as mitochondria, in the absence of another stimulus. Furthermore, modulation of glutathione or any Phase II enzyme is meant to include increased or decreased expression of the enzymes responsible for the production of glutathione, including glutathione transferase and glutamylcysteine synthetase, as well as increased or decreased expression of any Phase II enzyme.

As used herein, the phrase "increased or decreased expression" is used to mean an increase or decrease in the transcription rates of the genes responsible for coding the enzymes, resulting in an increase or decrease in the levels of mRNA for each gene, respectively. The phrase is also used to mean an increase or decrease in the levels of the protein or enzyme in the cell, independent of transcription rates. For example, an increase in degradation rate of an mRNA encoding the protein in question, without a change in the transcription rate, may result in a decrease in the levels of protein in the cell.

In a preferred embodiment, the methods of identifying agents that modulate intracellular levels of glutathione or Phase II enzymes are performed with an agent known to increase the intracellular levels of glutathione or intracellular levels of at least one Phase II detoxification enzyme.

In a more preferred embodiment, the methods of identifying the agents that modulate intracellular glutathione or Phase II enzymes are accomplished by using the control substances isothiocyanate, a glutathione precursor and a glucosinolate.

In a still more preferred embodiment, the methods of identifying agents that modulate intracellular glutathione or Phase II enzymes are accomplished by using control substances sulforaphane and a sulforaphane analog.

In a preferred embodiment, the methods of identifying agents that modulate intracellular levels of glutathione or Phase II enzymes are performed with an agent known to decrease the intracellular levels of glutathione or intracellular levels of at least one Phase II detoxification enzyme.

The present invention also provides a method of modulating intracellular levels of at least one Phase II detoxification enzyme in neuronal cells, said method comprising treating said neuronal cells with an agent that binds to glutathione to form a complex, wherein said complex modulates said intracellular levels of at least one Phase II detoxification enzyme.

The current invention also provides for a composition for use in the treatment of a degenerative disease, comprising a pharmaceutical excipient and a pharmaceutically effective amount of an agent that increases intracellular levels of glutathione or at least one Phase II detoxification enzyme.

In a preferred embodiment, the composition of the current invention comprises an agent selected from the group consisting of a glutathione precursor, an isothiocyanate and a glucosinolate. In a more preferred embodiment, the composition of the current invention comprises sulforaphane or a sulforaphane analog.

In another preferred embodiment, the composition of the current invention comprises an agent selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3(methylsulfonyl)cyclohexylmethylisothiocyanate and trans-3(methylsulfonyl)cyclohexylmethylisothiocyanate.

In still another preferred embodiment, the composition of the current invention comprises an agent selected from the group consisting of resveratrol, oltipraz, dimethylfumarate, 2(3)-tert-butyl-4-hydroxyanisole, 3,5-di-tert-butyl-4-hydroxytoluene and an analog thereof.

In a preferred embodiment, the composition of the current invention that is used to treat a degenerative disease is used to treat diabetes, chronic liver failure, Wilson's disease, congestive heart failure, atherosclerosis, and a neurological disorder.

In a more preferred embodiment, the composition of current invention is used to treat Alzheimer's Disease, Parkinson's Disease, Huntington's Disease, amyotrophic lateral sclerosis, epilepsy, myasthenia gravis, neuropathy, ataxia, dementia, chronic axonal neuropathy and stroke.

In another preferred embodiment, the composition of the current invention, which is used to treat degenerative diseases by increasing the levels of glutathione or any Phase II enzyme, is used to increase the enzymes selected from the group consisting of UDP-glucuronosyltransferases, sulfotransferases, phenol-O-methyltransferase, catechol-O-methyltransferase, histamine N-methyltransferase, nicotinamide N-methyltransferase, thiopurine methyltransferase, thiol methyltransferase, N-acetyltransferases, acyl-CoA synthetases, acyl-CoA:amino acid N-acyltransferases, aminoacyl-tRNA synthetases, glutathione synthetases, gamma glutamylcysteine synthetases, glutathione S-transferases, quinone reductases, heme oxygenases and rhodaneses.

Formulations and Methods of Administration A pharmaceutical composition of the invention is provided comprising an agent of the invention useful for treatment of a neurological disorder and a pharmaceutically acceptable carrier or excipient.

It will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion of hypertonic solutions which can transiently open the blood-brain barrier.

The blood-brain barrier (BBB) is a single layer of brain capillary endothelial cells that are bound together by tight junctions. The BBB excludes entry of many blood-borne molecules. In the invention, the agent can be modified for improved penetration of the blood-brain barrier using methods known in the art. Alternatively, a compound that increases permeability of the BBB can be administered to the subject. RMP-7, a synthetic peptidergic bradykinin agonist was reported to increase the permeability of the blood-brain barrier by opening the tight junctions between the endothelial cells of brain capillaries (Elliott, P. J. et al., *Exptl. Neurol.* 141:214–224 (1996)).

The invention further contemplates the use of prodrugs which are converted in vivo to the therapeutic compounds of the invention (Silverman, R. B., "The Organic Chemistry of Drug Design and Drug Action," Academic Press, Ch. 8 (1992)). Such prodrugs can be used to alter the biodistribution (e.g., to allow compounds which would not typically cross the blood-brain barrier to cross the blood-brain barrier) or the pharmacokinetics of the therapeutic compound. For example, an anionic group, e.g., a sulfate or sulfonate, can be esterified, e.g, with a methyl group or a phenyl group, to yield a sulfate or sulfonate ester. When the sulfate or sulfonate ester is administered to a subject, the ester is cleaved, enzymatically or non-enzymatically, to reveal the anionic group. Such an ester can be cyclic, e.g., a cyclic sulfate or sultone, or two or more anionic moieties can be esterified through a linking group. An anionic group can be esterified with moieties (e.g., acyloxymethyl esters) which are cleaved to reveal an intermediate compound which subsequently decomposes to yield the active compound. Furthermore, an anionic moiety can be esterified to a group which is actively transported in vivo, or which is selectively taken up by target organs. The ester can be selected to allow specific targeting of the therapeutic moieties to particular organs, as described below for carrier moieties.

The therapeutic compounds or agents of the invention can be formulated to cross the blood-brain-barrier, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs thus providing targeted drug delivery (Ranade, J., *Clin. Pharmacol.* 29:685 (1989)). Exemplary targeting moieties include folate or biotin (U.S. Pat. No. 5,416,016), mannosides (Umezawa et al., *Biochem. Biophys. Res. Comm.* 153:1038 (1988)), antibodies (Bloeman et al., *FEBS Lett.* 357:140 (1995); Owais et al, *Antimicrob. Agents Chemother.* 39:180 (1995)), surfactant protein A receptor (Briscoe et al., *Am. J.*

*Physiol.* 1233:134 (1995)), gp 120 (Schreier et al., *J. Biol. Chem.* 269:9090 (1994); Killion and Fidler, *Immunomethods* 4:273 (1994)).

The pharmaceutical composition can be administered orally, nasally, parenterally, intrasystemically, intraperitoneally, topically (as by drops or transdermal patch), bucally, or as an oral or nasal spray. By "pharmaceutically acceptable carrier" is intended, but not limited to, a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention can also contain adjuvants such as, but not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

In some cases, in order to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and l) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Topical administration includes administration to the skin or mucosa, including surfaces of the lung and eye. Compositions for topical administration, including those for inhalation, can be prepared as a dry powder which can be pressurized or non-pressurized. In nonpressurized powder compositions, the active ingredients in finely divided form can be used in admixture with a larger-sized pharmaceutically acceptable inert carrier comprising particles having a size, for example, of up to 100 $\mu$m in diameter. Suitable inert carriers include sugars such as lactose. Desirably, at least 95% by weight of the particles of the active ingredient have an effective particle size in the range of 0.01 to 10 $\mu$m.

Alternatively, the composition can be pressurized and contain a compressed gas, such as nitrogen or a liquefied gas propellant. The liquefied propellant medium and indeed the total composition is preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 et seq (1976)).

Dosaging

One of ordinary skill will appreciate that effective amounts of the agents of the invention can be determined empirically and can be employed in pure form or, where such forms exist, in pharmaceutically acceptable salt, ester or prodrug form. The agents can be administered to a subject, in need of treatment of a neurological disorder, as pharmaceutical compositions in combination with one or more pharmaceutically acceptable excipients. It will be understood that, when administered to a human patient, the total daily usage of the agents or composition of the present invention will be decided by the attending physician within the scope of sound medical judgement. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, satisfactory results are obtained by oral administration of the compounds at dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging can also be arranged in a patient specific manner to provide a predetermined concentration of the agents in the blood, as determined by techniques accepted and routine in the art (HPLC is preferred). Thus patient dosaging can be adjusted to achieve regular on-going blood levels, as measured by HPLC, on the order of from 50 to 1000 ng/ml, preferably 150 to 500 ng/ml.

It will be readily apparent to one of ordinary skill in the relevant arts that other suitable modifications and adaptations to the methods and applications described herein can be made without departing from the scope of the invention or any embodiment thereof.

The following Examples serves only to illustrate the invention, and are not to be construed as in any way to limit the invention.

EXAMPLES

Chronic excitotoxicity is thought to contribute to the characteristic motor neuron degeneration observed in amyotrophic lateral sclerosis (ALS). Organotypic spinal cord cultures defective in glutamate transport have been previously used to model chronic excitotoxicity in vitro to produce slow motor neuron degeneration. This system has proven to be effective as a preclinical screen for evaluating potential neuroprotective agents such as riluzole, insulin growth factor (IGF-1) and gabapentin, which were all shown to be protective, whereas ciliary neurotrophic factor (CNTF) and brain-derived neurotrophic factor (BDNF) both failed to protect against chronic motor neuron degeneration.

Example 1

Sulforphane Protects Motor Neurons from Chronic Glutamate Excitotoxicty

The general experimental procedure of THA-induced cytotoxicity was previously described (Ho T et al., Experimental Neurology, 161, 664–675, 2000), the contents of which are incorporated herein by reference. Rodent spinal cord tissue slices were treated with THA and/or sulforaphane. Sulforaphane was administered at concentrations at 0, 0.5 $\mu$M, 5 $\mu$M and 10 $\mu$M for 3 weeks, changing medium every three days. At the end of the experiment, each tissue slice was fixed and stained, and remaining neurons were counted.

Figure 1:
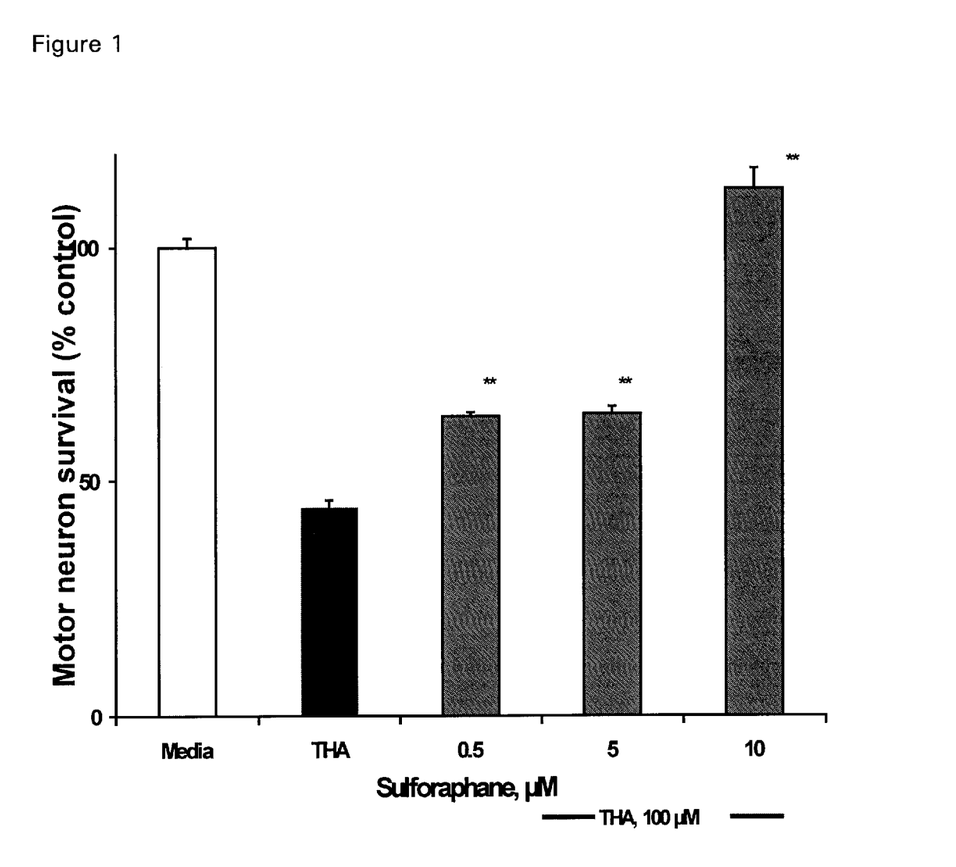
FIG. 1 depicts sulforaphane protecting motor neurons from chronic glutamate toxicity. **, p<0.01.

Sulforaphane significantly prevented THA-induced motor neuron death in the spinal cord explant (FIG. 1).

Example 2

Sulforaphane Elevates Spinal Cord Glutathione Levels

Figure 2:
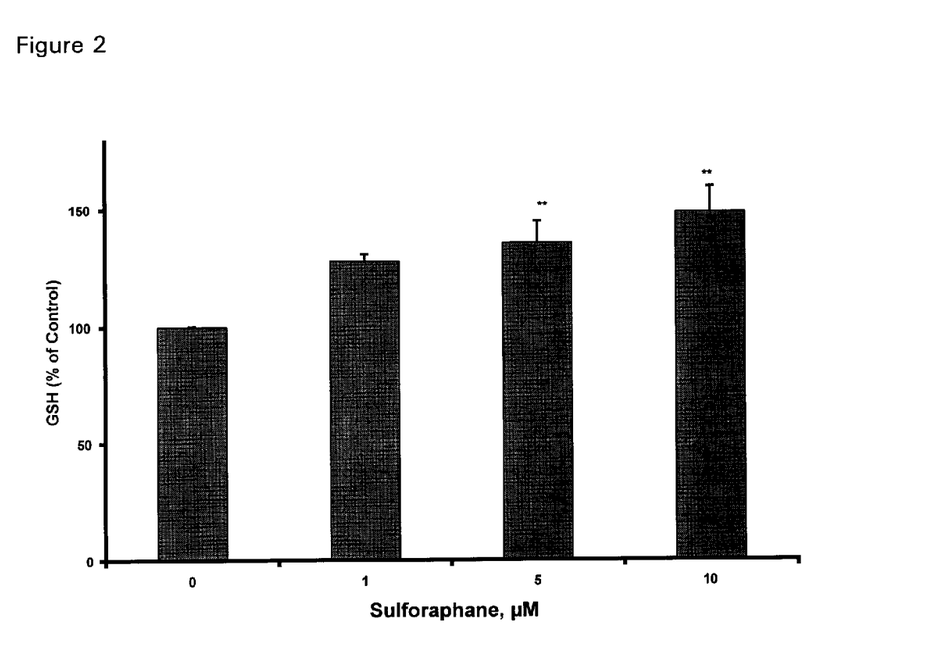
FIG. 2 depicts sulforaphane elevating organotypic spinal cord glutathione level. **, p<0.01.

Based on the above results, the level of GSH in spinal cord tissue treated with sulforphane was investigated. Rat spinal cord slices were similarly prepared and cultured as in the above example but without THA treatment. The tissues were cultured for one or two weeks and then incubated with 1 $\mu$M, 5, $\mu$M, or 10 $\mu$M, of sulphoraphane for 12 h, 24 h or 48 h. The tissue slices were then harvested and sonicated and assayed for total GSH content (Richie J P et al., Clinical Chemistry, 42, 64–70, 1996, the contents of which are incorporated herein by reference). GSH level in the sulforaphane-treated tissues was raised as much as 160% (FIG. 2).

These experiments indicate that sulforaphane is protective of neuronal cells and will be effective in ameliorating various neurological disorders.

Example 3

The Effects of Sulforaphane on Phase II Enzyme Activity in Spinal Cord Cultures

Mouse spinal cord cultures were prepared and cultured according to Rothstein, J D and Kuncl, R W. J. Neural Chem.

Figure 3:
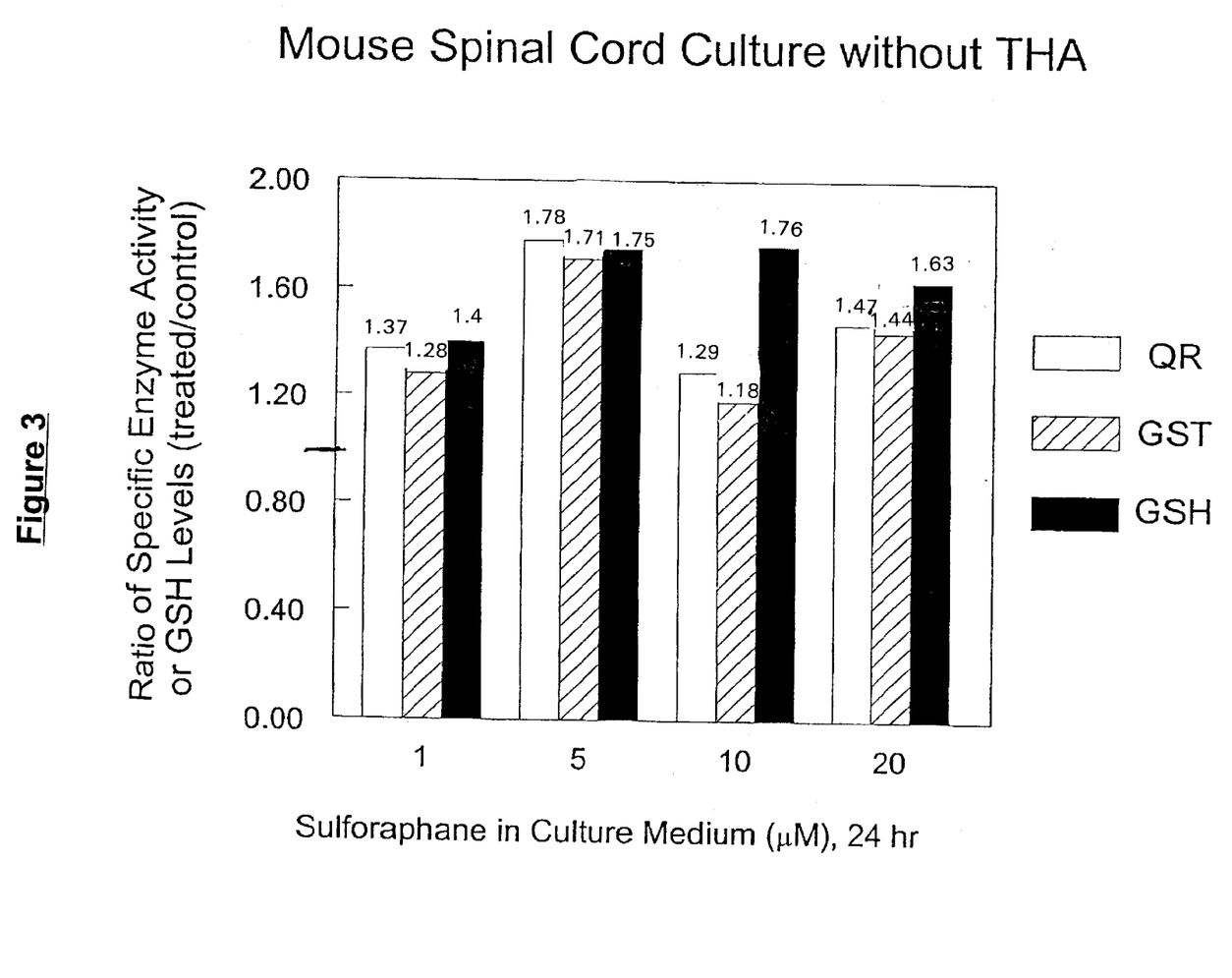
FIG. 3 depicts the ratio of specific enzyme activity or GSH levels in culture mediums treated with sulforaphane for 2 weeks.

65:643–651 (1995). Cultures were treated with sulforaphane for 24 hours at concentrations of 0,1 μm, 5 μm, 10 μm and 20 μm. After 24 hours the tissues were harvested and homogenized, and glutathione transferase (GST) activity was measured by the protocol as set forth in Richie, J. P. et al., Clinical Chemistry, (1996) 42:64–70 and quinone reductase (QR) activity was measured by the protocol as set forth in Zhang, et al., Proc. Natl. Acad. Sci. USA 89:2399–2403 (1992). Results indicate that sulforaphane induced the Phase II enzymes GST and QR (FIG. 3).

Example 4

The Effects of Sulforaphane on Phase II Enzyme Activity in Spinal Cord Cultures

Figure 4:
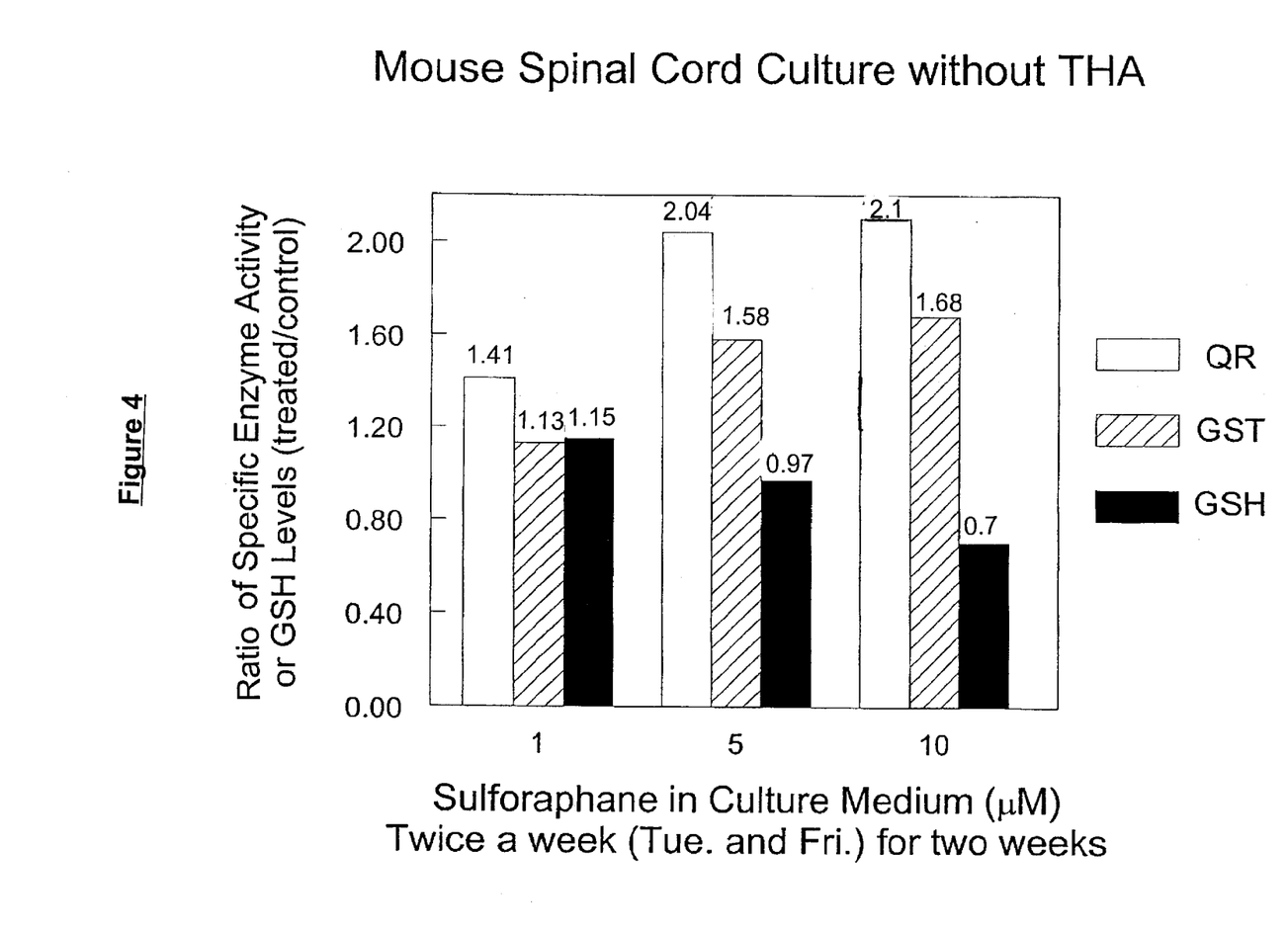
FIG. 4 depicts the ratio of specific enzyme activity or GSH levels in culture mediums treated with sulforaphane for 24 hours.

Mouse spinal cord cultures were prepared and cultured as above. Cultures were treated with sulforaphane for 2 weeks, twice a week, at concentrations of 1 μm, 5 μm and 10 μm. After 2 weeks the tissues were harvested and homogenized, and glutathione transferase activity was measured by the protocol as set forth in Richie, J. P. et al., Clinical Chemistry, (1996) 42:64–70 and quinone reductase activity was measured by the protocol as set forth in Zhang, et al., Proc. Natl. Acad. Sci. USA 89:2399–2403 (1992). Results indicate that sulforaphane induced the Phase II enzymes GST and QR (FIG. 4).

Example 5

The Effect of Sulforaphane in Transgenic Models of Alzheimer's Disease.

Method: Transgenic animals will be divided into four groups of 10 animals per group. The first group will receive 15 μm of sulforaphane orally every day. The second group will receive 15 μm of sulforaphane and N-acetylcysteine orally every day. The third group will receive N-acetylcysteine alone and a fourth group will receive vehicle control (CMC). Groups receiving N-acetylcysteine are required in this study because sulforaphane may transiently deplete intracellular glutathione levels before the induction of Phase II enzymes. Addition of N-acetylcysteine will boost the precursor for glutathione during this transitional induction period. Animals will begin treatment at weaning, and continue oral daily gavage of drug for a period of 8 to 10 months. Animals will be monitored with weekly weights. If selected transgenic animals have reliable behavior changes, complete behavioral testing will follow completion of the protocol. Animals will then be sacrificed and perfused. The brains will be harvested and amyloid deposits detected using immunohistochemistry and/or silver staining. Plaque burden in brain will be quantified using non-biased stereological methods. Brain GSH levels will also be determined.

Histopathology: One hemisphere of brains of a subset of mice (n=27; young, n=6; middle-aged, n=14; old, n=7) will be drop-fixed in formalin. Tissue will be mounted coronally and 30-μm sections collected using a cryostat. Every eighth section will be stored throughout the extent of the brain in antifreeze solution (30% glycerol/30% ethylene glycol in 40 mM NaPO$_4$) at –20° C. before immunostaining. Sections will be incubated with 3D6-biotinylated antibody overnight at 4° C. and then reacted with the horseradish peroxidase-avidin-biotin complex (Vector Laboratories) before development using 3,3'-diaminobenzidine as the chromagen. Amyloid deposition will be quantified automatically using an Image-Pro image analysis system. Video images of the brain will be captured, and outlines around the area of the hippocampus or cortex will be made to obtain a threshold optical density to discriminate staining from background. The amyloid 'plaque burden' is defined as the average percentage of hippocampal or cortical area covered by amyloid depositions over six sections.

ELISA: Cerebral Aβ levels will be assayed from formic-acid extracted hemi-brain sucrose homogenates using an ELISA method in which Aβ is trapped with either monoclonal antibody to Aβ$_{40}$ (JRF/cAb40/10) or Aβ$_{42}$ (JRF/cAb42/26) and then detected with horseradish peroxidase (HRP)-conjugated JRF/Abtot/17. The dilution of JRF/Abtot/17 and samples will be optimized to detect Aβ in the range of 50 to 800 fmol ml$^{-1}$. ELISA signals will be reported as the mean s.e.m. of four replica wells in fmol Aβ per mg total protein (determined with the BioRad DC protein assay), based on standard curves using synthetic Aβ$_{1-40}$ and Aβ$_{1-42}$ peptide standards (American Peptide Co. Sunnyvale, Calif.). Cerebral BβAPP levels will be analyzed in supernatant of brain as described.

Behavioral tests and data analysis: The cognitive status of the animals will be evaluated via a battery of tests including the modified Morris water maze or radial-arm water maze test, object recognition and Y-maze performance. The details of the behavioral tests will roughly follow those referenced. Animals will be tested prior to treatment as defined by each protocol, during treatment and just prior to termination of the mice.

Example 6

BBB Permeability and Bioavailability of Sulforaphane Compounds

Figure 5:
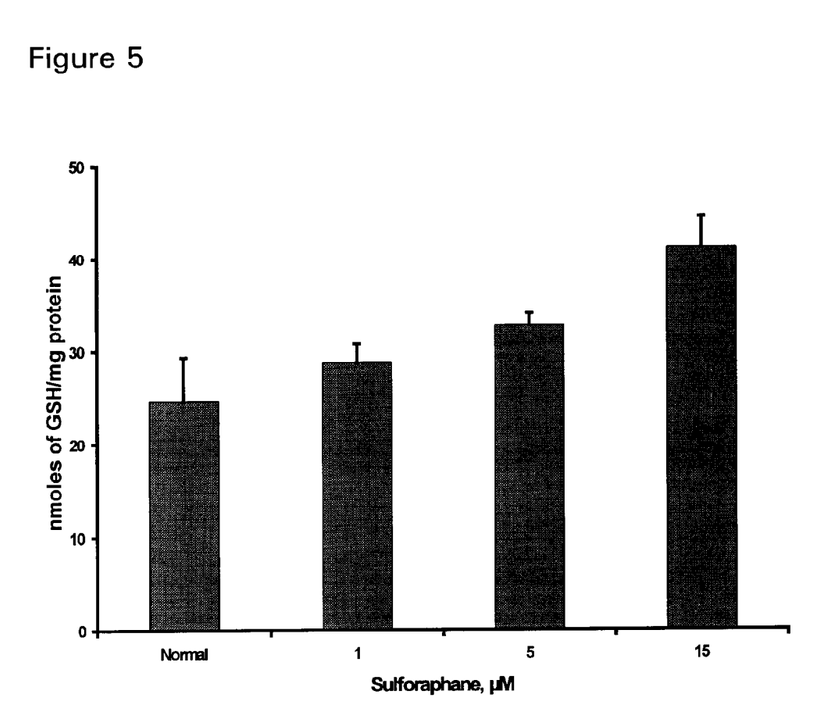
FIG. 5 depicts that oral administration of sulforaphane in mice potently elevates brain glutathione level. **, p<0.01.

Blood-brain barrier permeability of sulforaphane has been determined. Briefly, animals were dosed via daily oral gavage of the test or control compounds. After one week, the animals' whole brain were snap frozen and homogenized, and GSH levels were subsequently measured according to the protocol of Zhang, et al., Proc. Natl. Acad. Sci. USA 89:2399–2403 (1992). FIG. 5 shows the results of these experiments, demonstrating that sulforaphane was able to cross the BBB and elevate GSH levels in the brain.

To test for oral bio-availability, animals will receive a daily oral gavage of sulforaphane or control compounds. Blood will be collected and then mice will be euthanized at set intervals (1 weeks, 2 weeks, 1 month, 2 months, 6 months) after treatment begins. Brain, liver, heart tissues will also be harvested and analyzed for elevation of Phase II enzymes and GSH levels.

Example 7

The Effect of Sulforaphane in Transgenic Models of Amyotrophic Lateral Sclerosis (ALS)

SOD-G93 mice are transgenic mice that carry the same genetic mutation as the familial ALS patients. These mice are normal at birth but slowly develop motor neuron degeneration over time. By approximately 160 days, they will have developed severe paralysis because of the progressive loss of the motor neurons.

Method: Transgenic animals will be divided into four groups of 10 animals per group. The first group will receive 15 μm of sulforaphane orally every day. The second group will receive 15 μm of sulforaphane and N-acetylcysteine orally every day. The third group will receive N-acetylcysteine alone, and a fourth group will receive vehicle control (CMC). Groups receiving N-acetylcysteine are required in this study because sulforaphane may transiently deplete intracellular glutathione levels before the induction of Phase II enzymes. Addition of N-acetylcysteine will boost the precursor for glutathione during this transitional induction period. Animals will begin treatment at weaning, and continue oral daily gavage of the drugs. Onset of disease will be monitored by alteration on rotorod performance. Animals will be studied twice weekly starting at 1 month of age. A surrogate survival measure will be determined by the ability of the animals to right themselves after being placed on the cage on their backs. If they are unable to right themselves after 30 seconds, they will be considered dead. The survival and rotorod performance of each group of the animal will be compared. It is expected that sulforaphane or sulforaphane and N-acetylcystine will improve the survival of the animals compared to control. The brains will be harvested and brain GSH levels will also be determined.

References

1. Price D L, Tanzi R E, Borchelt D R and Sisodia S S. Alzheimer's disease: genetic studies and transgenic models. Annu Rev Genet 1998;32:461–93.

2. Selkoe D J, Yamazaki T. Citron M, Podlisny M B, Koo E H, Teplow D B and Haass C. The role of APP processing and trafficking pathways in the formation of amyloid beta-protein. Ann N Y Acad Sci 1996;777:57–64.

3. Jarrett J T and Lansbury P T, Jr. Seeding "one-dimensional crystallization" of amyloid: a pathogenic mechanism in Alzheimer's disease and scrapie? Cell 1993;73(6):1055–8.

4. Yankner B A. Mechanisms of neuronal degeneration in Alzheimer's disease. Neuron 1996;16(5):921–32.

5. Harkany T, Abraham I, Konya C, Nyakas C, Zarandi M, Penke B and Luiten P G. Mechanisms of beta-amyloid neurotoxicity: perspectives of pharmacotherapy. Rev Neurosci 2000;11 (4):329–82.

6. Hardy J. Amyloid, the presenilins and Alzheimer's disease. Trends Neurosci 1997;20(4):154–9.

7. Hardy J. The Alzheimer family of diseases: many etiologies, one pathogenesis? Proc Natl Acad Sci USA 1997;94(6):2095–7.

8. Younkin S G. Evidence that A beta 42 is the real culprit in Alzheimer's disease. Ann Neurol 1995;37(3):287–8.

9. Selkoe D J. Toward a comprehensive theory for Alzheimer's disease. Hypothesis: Alzheimer's disease is caused by the cerebral accumulation and cytotoxicity of amyloid beta-protein. Ann N Y Acad Sci 2000;924:17–25.

10. Hensley K, Hall N, Subramaniam R, Cole P, Harris M, Aksenov M, Aksenova M, Gabbita S P, Wu J F, Carney J M and et al. Brain regional correspondence between Alzheimer's disease histopathology and biomarkers of protein oxidation. J Neurochem 1995;65(5):2146–56.

11. Mecocci P, MacGarvey U and Beal M F. Oxidative damage to mitochondrial DNA is increased in Alzheimer's disease. Ann Neurol 1994;36(5):747–51.

12. Palmer A M and Burns M A. Selective increase in lipid peroxidation in the inferior temporal cortex in Alzheimer's disease. Brain Res 1994;645(1–2):338–42.

13. Lovell M A and Markesbery W R. Ratio of 8-Hydroxyguanine in Intact DNA to Free 8-Hydroxyguanine Is Increased in Alzheimer Disease Ventricular Cerebrospinal Fluid. Arch Neurol 2001;58(3): 392–396.

14. Aksenov M Y, Aksenova M V, Butterfield D A, Geddes J W and Markesbery W R. Protein oxidation in the brain in Alzheimer's disease. Neuroscience 2001;103(2): 373–83.

15. Behl C, Davis J B, Lesley R and Schubert D. Hydrogen peroxide mediates amyloid beta protein toxicity. Cell 1994;77(6):817–27.

16. Varadarajan S, Yatin S, Aksenova M and Butterfield D A. Review: Alzheimer's amyloid beta-peptide-associated free radical oxidative stress and neurotoxicity. J Struct Biol 2000;130(2–3):184–208.

17. Markesbery W R. The role of oxidative stress in Alzheimer disease. Arch Neurol 1999;56(12):1449–52.

18. Pappolla M A, Chyan Y J, Omar R A, Hsiao K, Perry G, Smith M A and Bozner P. Evidence of oxidative stress and in vivo neurotoxicity of beta-amyloid in a transgenic mouse model of Alzheimer's disease: a chronic oxidative paradigm for testing antioxidant therapies in vivo. Am J Pathol 1998;152(4):871–7.

19. Smith M A, Hirai K, Hsiao K, Pappolla M A, Harris P L, Siedlak S L, Tabaton M and Perry G. Amyloid-beta deposition in Alzheimer transgenic mice is associated with oxidative stress. J Neurochem 1998;70(5):2212–5.

20. Sano M, Ernesto C, Thomas R G, Klauber M R, Schafer K, Grundman M, Woodbury P, Growdon J, Cotman C W, Pfeiffer E, Schneider L S and Thal L J. A controlled trial of selegiline, alpha-tocopherol, or both as treatment for Alzheimer's disease. The Alzheimer's Disease Cooperative Study. N Engl J Med 1997;336(17):1216–22.

21. Eckert A, Steiner B, Marques C, Leutz S, Romig H, Haass C and Muller W E. Elevated vulnerability to oxidative stress-induced cell death and activation of caspase-3 by the Swedish amyloid precursor protein mutation. J Neurosci Res 2001;64(2):183–192.

22. Takahashi M, Dore S, Ferris C D, Tomita T, Sawa A, Wolosker H, Borchelt D R, lwatsubo T, Kim S H, Thinakaran G, Sisodia S S and Snyder S H. Amyloid precursor proteins inhibit heme oxygenase activity and augment neurotoxicity in Alzheimer's disease. Neuron 2001;28(2): 461–73.

23. Masliah E, Sisk A, Mallory M, Mucke L, Schenk D and Games D. Comparison of neurodegenerative pathology in transgenic mice overexpressing V717F beta-amyloid precursor protein and Alzheimer's disease. J Neurosci 1996;16 (18):5795–811.

24. Chen G, Chen K S, Knox J, Inglis J, Bernard A, Martin S J, Justice A, McConlogue L, Games D, Freedman S B and Morris R G. A learning deficit related to age and beta-amyloid plaques in a mouse model of Alzheimer's disease. Nature 2000;408(6815):975–9.

25. Wisniewski H M, Bancher C, Barcikowska M, Wen G Y and Currie J. Spectrum of morphological appearance of amyloid deposits in Alzheimer's disease. Acta Neuropathol 1989;78(4):337–47.

26. Citron M, Westaway D, Xia W, Carlson G, Diehl T, Levesque G, Johnson-Wood K, Lee M, Seubert P, Davis A, Kholodenko D, Motter R, Sherrington R, Perry B, Yao H, Strome R, Lieberburg I, Rommens J, Kim S, Schenk D, Fraser P, St George Hyslop P and Selkoe D J. Mutant presenilins of Alzheimer's disease increase production of 42-residue amyloid beta-protein in both transfected cells and transgenic mice. Nat Med 1997;3(1):67–72.

27. Morgan D, Diamond D M, Gottschall P E, Ugen K E, Dickey C, Hardy J, Duff K, Jantzen P, DiCarlo G, Wilcock D, Connor K, Hatcher J, Hope C, Gordon M and Arendash G W. A beta peptide vaccination prevents memory loss in an animal model of Alzheimer's disease. Nature 2000;408 (6815):982–5.

28. Holcomb L A, Gordon M N, Jantzen P, Hsiao K, Duff K and Morgan D. Behavioral changes in transgenic mice expressing both amyloid precursor protein and presenilin-1 mutations: lack of association with amyloid deposits. Behav Genet 1999;29(3):177–85.

29. Talalay, P. Chemoprotection against cancer by induction of Phase 2 enzymes. BioFactors 2000; 12:5–11.

30. Prestera, T, Talalay, P, Alam, J., Akn, Y. l., Lee, P. J., Choi, A. M. K. Parallel induction of heme oxygenase-1 and chemoprotective Phase 2 enzymes by electrophiles and antioxidants: regulation by upstream antioxidant-responsive elements. Mol. Med. 1995; 1:827–837.

31. Primiano, T., Kensler, T. W., Kuppusamy, P., Zweier, J. L., Sutter, T. R. Induction of hepatic heme oxygenase and ferritin in rats by cancer chemopreventive dithiolethiones. Carcinogenesis 1996; 17:2291–2296.

What is claimed is:

1. A method of treating a subject in need of treatment of Parkinson's Disease, said method comprising administering to said subject a pharmaceutically effective amount of a compound that elevates intracellular levels of glutathione or intracellular levels of at least one Phase II detoxification enzyme in diseased tissue of said subject, wherein said compound is selected from the group consisting of sulforaphane and a sulforaphane analog.

2. The method of claim 1, wherein said sulforaphane analog is selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3(methylsulfonyl)cyclohexylmethylisothiocyanate and trans-3(methylsulfonyl)cyclohexylmethylisothiocyanate.

3. A method of inhibiting cell death in neuronal cells comprising treating said neuronal cells with an agent that increases intracellular levels of glutathione or intracellular levels of at least one Phase II detoxification enzyme, wherein said agent is selected from the group consisting of sulforaphane and a sulforaphane analog.

4. The method of claim 3, wherein said sulforaphane analog is selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3(methylsulfonyl)cyclohexylmethylisothiocyanate and trans-3(methylsulfonyl)cyclohexylmethylisothiocyanate.

5. A method of modulating intracellular levels of at least one Phase II detoxification enzyme in neuronal cells, said method comprising treating said neuronal cells with an agent that binds to glutathione to form a complex, wherein said complex modulates said intracellular levels of at least one Phase II detoxification enzyme, and wherein said agent is selected from the group consisting of sulforaphane and a sulforaphane analog.

6. The method of claim 5, wherein said sulforaphane analog is selected from the group consisting of 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3(methylsulfonyl)cyclohexylmethylisothiocyanate and trans-3(methylsulfonyl)cyclohexylmethylisothiocyanate.

* * * * *

UNITED STATES PATENT AND TRADEMARK OFFICE
CERTIFICATE OF CORRECTION

PATENT NO. : 6,812,248 B2
DATED : November 2, 2004
INVENTOR(S) : Yuesheng Zhang, Tony W. Ho and Yun Li It is certified that error appears in the above-identified patent and that said Letters Patent is hereby corrected as shown below:

<u>Column 1,</u>
Line 5, insert the following paragraph,
-- The U.S. Government has a paid-up license in this invention and the right in limited circumstances to require the patent owner to license others on reasonable terms as provided for by the terms of Grant Numbers CA44530 and NS31528 awarded by the National Institute of Health. --

Signed and Sealed this

Tenth Day of May, 2005

JON W. DUDAS
*Director of the United States Patent and Trademark Office*